(12) United States Patent
Cassivi (10) Patent No.: US 9,421,396 B2
(45) Date of Patent: Aug. 23, 2016

(54) BRACHYTHERAPY AND BUTTRESS ELEMENT CO-DELIVERY

(71) Applicant: Mayo Foundation for Medical Education and Research, Rochester, MN (US)

(72) Inventor: Stephen D. Cassivi, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 126 days.

(21) Appl. No.: 14/019,277

(22) Filed: Sep. 5, 2013

(65) Prior Publication Data

US 2014/0066688 A1 Mar. 6, 2014

Related U.S. Application Data

(60) Provisional application No. 61/696,985, filed on Sep. 5, 2012.

(51) Int. Cl.
*A61N 5/10* (2006.01)

(52) U.S. Cl.
CPC ........ *A61N 5/1007* (2013.01); *Y10T 29/49826* (2015.01)

(58) Field of Classification Search
CPC .............. Y10T 29/49826; A61N 5/1007
See application file for complete search history.

(56) References Cited

U.S. PATENT DOCUMENTS

| | | | |
|---|---|---|---|
| 4,754,745 A | 7/1988 | Horowitz | |
| 5,030,195 A * | 7/1991 | Nardi | G21G 4/08 600/7 |
| 5,415,334 A | 5/1995 | Williamson, IV et al. | |
| 5,468,253 A | 11/1995 | Bezwada et al. | |
| 5,597,107 A | 1/1997 | Knodel et al. | |
| 5,752,965 A | 5/1998 | Francis et al. | |
| 5,810,855 A | 9/1998 | Rayburn et al. | |
| 5,906,573 A | 5/1999 | Aretz | |
| 5,919,184 A | 7/1999 | Tilton, Jr. | |
| 6,592,597 B2 | 7/2003 | Grant et al. | |
| 6,656,193 B2 | 12/2003 | Grant et al. | |
| 6,704,210 B1 | 3/2004 | Myers | |
| 6,793,798 B2 | 9/2004 | Chan et al. | |
| 6,939,358 B2 | 9/2005 | Palacios et al. | |

(Continued)

FOREIGN PATENT DOCUMENTS

| | | |
|---|---|---|
| WO | WO 97/03614 A1 | 2/1997 |
| WO | WO 2008/057281 A2 | 5/2008 |
| WO | WO 2008/057281 A3 | 7/2008 |

OTHER PUBLICATIONS

"Brachytherapy," Wikipedia, the free encyclopedia [online]. retrieved Aug. 6, 2008. Available online: <URL: http://en.wikipedia.org/wiki/Brachytherapy>, 2 pgs.

(Continued)

*Primary Examiner* — Christine H Matthews
*Assistant Examiner* — Joshua D Lannu
(74) *Attorney, Agent, or Firm* — Mueting, Raasch & Gebhardt, P.A.

(57) ABSTRACT

Brachytherapy delivery devices and buttress elements are described herein, along with methods of assembling the brachytherapy devices and the buttress elements for co-delivery of the brachytherapy delivery devices and buttress elements are described herein.

20 Claims, 3 Drawing Sheets (56) References Cited

U.S. PATENT DOCUMENTS

| | | |
|---|---|---|
| 7,147,138 B2 | 12/2006 | Shelton, IV |
| 7,377,928 B2 | 5/2008 | Zubik et al. |
| 7,604,586 B2 | 10/2009 | Wazer et al. |
| 7,972,260 B2 | 7/2011 | Wazer et al. |
| 8,267,849 B2 | 9/2012 | Wazer et al. |
| 2004/0093029 A1 | 5/2004 | Zubik et al. |
| 2006/0173470 A1 | 8/2006 | Oray et al. |
| 2007/0128243 A1 | 6/2007 | Serafica et al. |
| 2007/0179528 A1 | 8/2007 | Soltz et al. |
| 2007/0246505 A1 | 10/2007 | Pace-Floridia et al. |
| 2008/0109034 A1 | 5/2008 | Mather et al. |
| 2009/0001122 A1 | 1/2009 | Prommersberger et al. |
| 2009/0012347 A1* | 1/2009 | Helle ............... A61M 37/0069 600/7 |
| 2009/0125041 A1 | 5/2009 | Dudai |
| 2010/0059570 A1 | 3/2010 | Ostapoff et al. |
| 2012/0123535 A1* | 5/2012 | Alejandro ............ A61F 2/12 623/8 |
| 2012/0125792 A1 | 5/2012 | Cassivi |

OTHER PUBLICATIONS

Chen et al., "Intraoperative $^{125}$I Brachytherapy for High-Risk Stage I Non-Small Cell Lung Carcinoma," *Int. J. Radiation Oncology Biol. Phys.*, 1999;44(5):1057-1063.

Downey et al., "Functional Assessment of a New Staple Line Reinforcement in Lung Resection," *J. Surg. Res.*, Mar. 2006; 131(1): 49-52. Available online Aug. 29, 2005.

Gore Seamguard® Biosorbable Staple Line Reinforcement, W.L. Gore & Associates, Inc., Flagstaff, AZ; Feb. 2008 [online]. Retrieved Jul. 15, 2011. Available online: <URL: http://www.goremedical.com/resources/dam/assets/AM2903-EN2__covidien__OR__card.pdf>, 2 pgs.

Santos et al., "Comparison between sublobar resection and $^{125}$Iodine brachytherapy after sublobar resection in high-risk patients with Stage I non-small-cell lung cancer," *Surgery*, Oct. 2003; 134(4): 691-697.

Voynov et al, "Intraoperative $^{125}$I Vicryl mesh brachytherapy after sublobar resection for high-risk stage I nonsmall cell lung cancer," *Brachytherapy*, Dec. 2005; 4(4): 278-285.

* cited by examiner

BRACHYTHERAPY AND BUTTRESS ELEMENT CO-DELIVERY

RELATED APPLICATION

The present application claims the benefit under 35 U.S.C. §119(e) of U.S. Provisional Application Ser. No. 61/696,985, titled BRACHYTHERAPY AND BUTTRESS ELEMENT CO-DELIVERY, filed on Sep. 5, 2012, which is incorporated herein by reference in its entirety.

Devices and methods for delivering brachytherapy along with a buttress element used in surgical fastening of anatomical tissue are described herein.

Surgical fastening of anatomical tissue may be performed using, for example, a surgical fastening instrument (e.g., a surgical stapler). In some circumstances, it may also be desired to provide, for example, radiation to a localized region near surgically fastened anatomical tissue. Radiation may be provided in order to, for example, treat cancer.

In some medical procedures, localized application of radiation to anatomical tissue is desired. One method of applying radiation to anatomical tissue includes placing radioactive material (e.g., brachytherapy seeds) near the anatomical tissue to be irradiated. Brachytherapy is a form of radiotherapy wherein a radioactive source is sealed and placed in or near an area to be treated. When brachytherapy is planned, the brachytherapy seeds may be sewn by hand onto a piece of mesh. During a lung resection surgery, lung tissue is resected followed by the mesh (with the brachytherapy seeds thereon) being manually sutured to the non-resected lung tissue along the staple line. Such manual attachment of the brachytherapy seeds is time consuming and technically challenging.

SUMMARY

Brachytherapy delivery devices and buttress elements are described herein, along with methods of assembling the brachytherapy devices and the buttress elements for co-delivery of the brachytherapy delivery devices and buttress elements are described herein. The devices and methods may be used in, for example, a surgical procedure (e.g., a lung resection). Co-delivery of radioactive material and a buttress element may provide various advantages, such as reducing surgical time, reducing patient recovery time, and reducing technical difficulty of surgery. In some embodiments, a medically useful agent may be provided in addition to the radioactive material.

The buttress elements described herein, with or without any brachytherapy delivery devices as described herein, may be delivered by any suitable equipment, methods, and/or techniques as described in, e.g., U.S. Patent Application No. US 2012/0125792, titled DEVICES, KITS AND METHODS FOR SURGICAL FASTENING.

A buttress element may be a component of a surgical fastener system, which may include surgical fasteners including, but not limited to, staples. In one or more embodiments in which one or more staples are used as one or more surgical fasteners, a buttress element may be a staple line buttress element. Buttress elements may be used in, for example, surgical procedures that involve, for example, resection of anatomical tissue. Buttress elements may provide reinforcement of surgically fastened anatomical tissue at, for example, a staple line. See, e.g., Downey et al., "Functional Assessment of a New Staple Line Reinforcement in Lung Resection," *J. Surg. Res.*, 131 (1): 49-52 (March 2006). In one or more embodiments, buttress elements may provide increased hemostasis and aerostasis (reduction of air leaks) in surgically fastened anatomical tissue.

As used herein, anatomical tissue refers to any tissue of an animal (e.g., fish, amphibian, reptile, bird, or mammal) that may be surgically fastened (e.g., stapled). In one or more embodiments, the anatomical tissue includes lung tissue (e.g., diseased lung tissue) of which a portion may be or may have been resected. In one or more embodiments, the anatomical tissue may include tissues proximal to cancerous cells and/or tumors.

Buttress elements may be used in a variety of different procedures including, for example, lung resection surgery wherein portions of the lungs are surgically fastened with, for example, a surgical stapler. In the present disclosure, a wide variety of staplers may be used including, but not limited to, those adapted for use in endoscopic surgery, such as those disclosed in U.S. Pat. No. 5,597,107 (Knodel et al.) and U.S. Pat. No. 6,656,193 (Grant et al.) and those staplers designed for open procedures, such as those disclosed in U.S. Pat. No. 5,415,334 (Williamson, IV et al.) and PCT Publication No. WO 2008/057281 (Stopek).

In a first aspect, one or more embodiments of a brachytherapy delivery device as described herein may include: a carrier line comprising a length extending between a first end and a second end, wherein radioactive material is distributed along the length of the carrier line; and a stylet extending from a base to a tip, wherein the first end of the carrier line is attached to the stylet proximate the base of the stylet, and wherein the stylet is configured to be advanced tip-first through an opening and wherein further advancement of the stylet draws the carrier line through the opening.

In one or more embodiments of a brachytherapy delivery device of the first aspect, the stylet comprises a bending stiffness greater than a bending stiffness of the carrier line.

In one or more embodiments of a brachytherapy delivery device of the first aspect, the carrier line is configured to wrap around a right circular cylinder having a diameter of less than half of a length of the stylet between the base and the tip of the stylet.

In one or more embodiments of a brachytherapy delivery device of the first aspect, the radioactive material comprises a plurality of radioactive seeds attached to the carrier line at discrete locations. In one or more embodiments, the plurality of radioactive seeds are adhesively attached to the carrier line. In one or more embodiments, the plurality of radioactive seeds are encased within the carrier line.

In one or more embodiments of a brachytherapy delivery device of the first aspect, the carrier line is selected from the group consisting of: suture material, ribbon, wire, and cable.

In a second aspect, one or more embodiments of a buttress element as described herein may include: a body in the form of a sheet comprising a thickness, wherein the thickness is measured between a first major surface and a second major surface, and wherein the body is constructed of one or more biocompatible materials; and a channel formed in the body, the channel extending from a first end to a second end, and wherein the channel is located between the first major surface and the second major surface.

In one or more embodiments of a buttress element of the second aspect, the buttress element comprises a width measured between a first side and a second side, and the channel extends from the first side to the second side of the buttress element.

In one or more embodiments of a buttress element of the second aspect, the buttress element comprises a width measured between a first side and a second side, and the channel extends over a channel distance that is less than the entire width of the buttress element.

In one or more embodiments of a buttress element of the second aspect, the channel comprises a first opening proximate the first end of the channel. In one or more embodiments, the channel comprises a second opening proximate the second end of the channel.

In one or more embodiments of a buttress element of the second aspect, the channel is formed between two layers of buttress material attached together along opposing edges of the channel.

In one or more embodiments of a buttress element of the second aspect, the buttress element comprises a plurality of channels formed in the body, wherein each channel of the plurality of channels extends from a first end to a second end and is located between the first major surface and the second major surface of the body. In one or more embodiments, the plurality of channels are aligned with each other.

In one or more embodiments of a buttress element of the second aspect, the biocompatible material comprises bioresorbable material.

In a third aspect, one or more embodiments of a buttress element as described herein may include: a body in the form of a sheet comprising a thickness, wherein the thickness is measured between a first major surface and a second major surface, wherein the body comprises a width measured between a first side and a second side, and wherein the body is constructed of one or more biocompatible materials; and a plurality of openings formed through the thickness of the body between the first major surface and the second major surface, wherein the plurality of openings comprises a first opening proximate the first side of the body and a second opening proximate the second side of the body.

In one or more embodiments of a buttress element of the third aspect, the plurality of openings comprises one or more intermediate openings located between the first side of the body and the second side of the body.

In one or more embodiments of a buttress element of the third aspect, the plurality of openings comprises one or more intermediate openings located between the first side of the body and the second side of the body, and at least one of the one or more intermediate openings is located along a straight line extending between the first opening and the second opening when the buttress element is in a flat configuration.

In a fourth aspect, a method of assembling a buttress element with radioactive material as described herein may include: inserting a brachytherapy delivery device as described herein into a channel in a buttress element, wherein the buttress element comprises a body in the form of a sheet comprising a thickness, wherein the thickness is measured between a first major surface and a second major surface, and wherein the body is constructed of one or more biocompatible materials, and wherein the channel is formed in the body, the channel extending from a first end to a second end, and wherein the channel is located between the first major surface and the second major surface of the buttress element; advancing the tip of the stylet of the brachytherapy delivery device through the channel until at least a portion of the radioactive material is located in the channel; and separating the carrier line from the stylet.

In a fifth aspect, a method of assembling a buttress element with radioactive material as described herein may include: inserting a brachytherapy delivery device as described herein through a first opening in a buttress element, wherein buttress element comprises a body in the form of a sheet comprising a thickness, wherein the thickness is measured between a first major surface and a second major surface, wherein the body comprises a width measured between a first side and a second side, and wherein the body is constructed of one or more biocompatible materials, and wherein the first opening is formed through the thickness of body between the first major surface and the second major surface; advancing the stylet of the brachytherapy delivery device through the channel until at least a portion of the radioactive material passes through the first opening; advancing the stylet of the brachytherapy delivery device through a second opening formed through the thickness of body between the first major surface and the second major surface, wherein the carrier line extends between the first opening and the second opening; and separating the carrier line from the stylet.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a channel may be used to refer to one, two, three or more channels.

The term "and/or" means one or all of the listed elements or a combination of any two or more of the listed elements.

The above summary is not intended to describe each embodiment or every implementation of the devices and methods described herein. Rather, a more complete understanding of the devices and methods described herein will become apparent and appreciated by reference to the following Description of Illustrative Embodiments and claims in view of the accompanying figures.

DESCRIPTION OF ILLUSTRATIVE EMBODIMENTS

In the following description of illustrative embodiments, reference is made to the accompanying figures which form a part hereof, and in which are shown, by way of illustration, specific embodiments in which the devices and/or methods may be practiced. It is to be understood that other embodiments may be utilized and structural changes may be made without departing from the scope of the present invention.

The devices and methods described herein may be used to deliver provide radioactive material in a brachytherapy delivery device and a buttress element in a variety of procedures that typically eventually involve the use of a stapler to fasten the buttress material to tissue, with the radioactive material in the brachytherapy delivery devices described herein being provided to deliver radiation energy to the tissue. In some embodiments, one or more medically useful agents may be provided in addition to the radioactive material of the brachytherapy delivery devices.

Brachytherapy Delivery Devices

Figure 1:
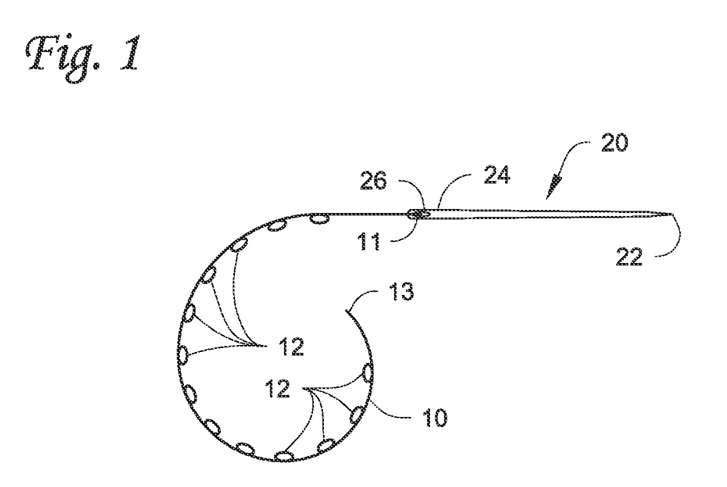
FIG. 1 depicts one illustrative embodiment of a brachytherapy delivery device as described herein.

With reference to FIG. 1, one illustrative embodiment of a brachytherapy delivery device is depicted. The brachytherapy delivery device includes a carrier line 10 attached to a stylet 20. The carrier line 10 has a length extending between a first end 11 and a second end 13. Radioactive material is distributed along the length of the carrier line 10. In the depicted embodiment, the radioactive material is provided in the form of radioactive brachytherapy seeds 12 attached to the carrier line 10, although the radioactive material supplied in the brachytherapy delivery devices described herein could be provided in other forms, such as, e.g., fibers, etc.

The brachytherapy delivery device includes a stylet 20 having a base 24 and a tip 22. The first end 11 of the carrier line 10 is attached to the stylet 20 proximate the base 24 of the stylet 20. In the depicted embodiment, the stylet 20 includes an opening 26, such that the carrier line 10 could be tied to the stylet 20 using the opening 26. Many other alternative techniques for attaching the carrier line 10 to the stylet 20 could be used, e.g., adhesives, welding (chemical and/or thermal), mechanical fasteners (e.g., clamps, etc.).

The stylet 20 is configured to be advanced tip-first through an opening (e.g., while grasping the base 24 of the stylet 20). Further advancement of the stylet 20 through the opening draws the carrier line 10 through the opening (in a manner similar to, e.g., sewing with a needle and thread).

In one or more embodiments, the stylet 20 has a bending stiffness greater than a bending stiffness of the carrier line 10. In other words, a selected force directed through the stylet 20 in direction transverse to an axis extending through a center of the stylet 20 from the base 24 to the tip 22 would result in less deflection in the stylet 20 than the deflection that would occur in the carrier line 10 if the same force were directed through the carrier line 10 in a direction transverse to an axis extending through a center of the carrier line 10 when the carrier line is arranged along a straight line from the first end 11 to the second end 13.

In one or more embodiments, the carrier line 10 may be flexible such that it can be manipulated to, e.g., follow a curved path in a manner similar to a thread or ribbon. In one or more embodiments, the flexibility of the carrier line 10 may be such that the carrier line 10 is capable of being wrapped around a right circular cylinder having a diameter of less than half of a length of the stylet 20 (where the length of the stylet 20 is measured from the base 24 to the tip 22).

The radioactive material provided in the brachytherapy delivery devices described herein may be any suitable radioactive material for medical applications and include a wide variety of radioactive elements. Medical applications for which radioactive material may be used include, but are not limited to, treatment of anatomical tissues, including, but not limited to cancerous cells and/or tumors, wherein the cancers may include lung cancer, thymic cancer, thymoma, metastatic cancers, metastatic sarcomas, etc.

Radioactive material may include, but is not limited to, brachytherapy seeds appropriate for a medical application. Brachytherapy seeds may be commercially available from Oncura (Arlington Heights, Ill.), BestMedical International Inc. (Springfield, Va.), and other suppliers. Suitable radioactive materials may include, but are not limited to, iodine (e.g., iodine-125), palladium (e.g., palladium-103), and combinations thereof. Some examples of brachytherapy seeds and some methods of using same may be found in, for example, Santos et al., "Comparison between sublobar resection and $^{125}$Iodine brachytherapy after sublobar resection in high-risk patients with Stage I non-small-cell lung cancer," *Surgery* 134 (4): 691-697 (October 2003); and Voynov et al., "Intraoperative $^{125}$I Vicryl mesh brachytherapy after sublobar resection for high-risk stage I nonsmall cell lung cancer," *Brachytherapy* 4 (4): 278-285 (December 2005). Any suitable radioactive material may be chosen by one of skill in the art to, for example, provide an appropriate duration and/or intensity of radiation treatment.

The radioactive material is attached to the carrier line such that the amount of radioactive material and the distribution of radioactive material provide, for example, a prescribed dosage of radiation to anatomical tissue. In the illustrative embodiment depicted in FIG. 1, the radioactive material of the carrier line 10 may be in the form of radioactive seeds 12 attached to the carrier line 10 at discrete locations.

The radioactive material may be distributed on a carrier line in a regular or irregular pattern. In one or more embodiments, radioactive material (e.g., brachytherapy seeds) is arranged in a pattern wherein the radioactive material is regularly spaced in a repeating geometric pattern (e.g., parallelograms, triangles, circles, etc.). For example, the brachytherapy seeds 12 of the illustrative embodiment of FIG. 1 are arranged in a regularly repeating pattern on the carrier line 10. In one or more embodiments, the radioactive material is not evenly distributed across the carrier element. In embodiments including more than one brachytherapy delivery device, the distribution of radioactive material on the carrier lines of each of the brachytherapy delivery devices may be the same as the distribution on another carrier line or may be different than the distribution of radioactive material on another carrier line.

Any suitable technique for attaching the radioactive material to the carrier line of a brachytherapy delivery device described herein may be used. Some potentially suitable attachment techniques may include, e.g., adhering, sewing, embedding, etc. In one or more embodiments, radioactive material may, for example, be provided in the form of a fibrous material that could, for example, constitute a portion of a carrier line of a brachytherapy delivery device.

Figure 2:
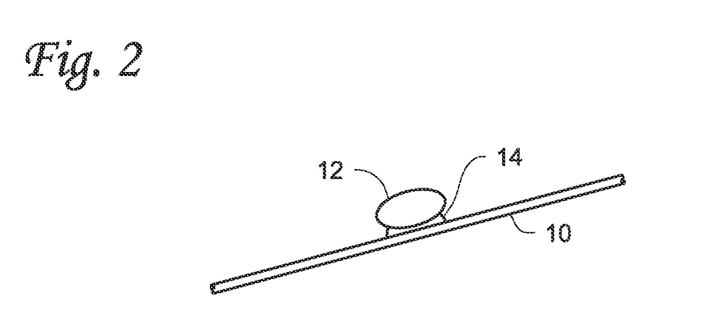
FIG. 2 is an enlarged view of a portion of the brachytherapy delivery device of FIG. 1 depicting a brachytherapy seed attached to a carrier line.

In the illustrative embodiment depicted in FIGS. 1 and 2, the radioactive seeds 12 are adhesively attached to the carrier line 10 using adhesive 14. An alternative technique for attaching brachytherapy seeds to a carrier line is depicted in the cross-sectional view of FIG. 3, in which the seed 112 is encased or embedded within the carrier line 110 (which, in the depicted embodiment includes layers 115 and 116 between which the seed 112 is located).

The carrier lines used in the brachytherapy delivery devices described herein may be constructed of any suitable material or materials, including, e.g., polymers, metals, organic materials (e.g., gut, cotton, etc.). In one or more embodiments, the carrier lines may be selected from the group consisting of: suture material, ribbon, wire, and cable.

Buttress Elements

Figure 4:
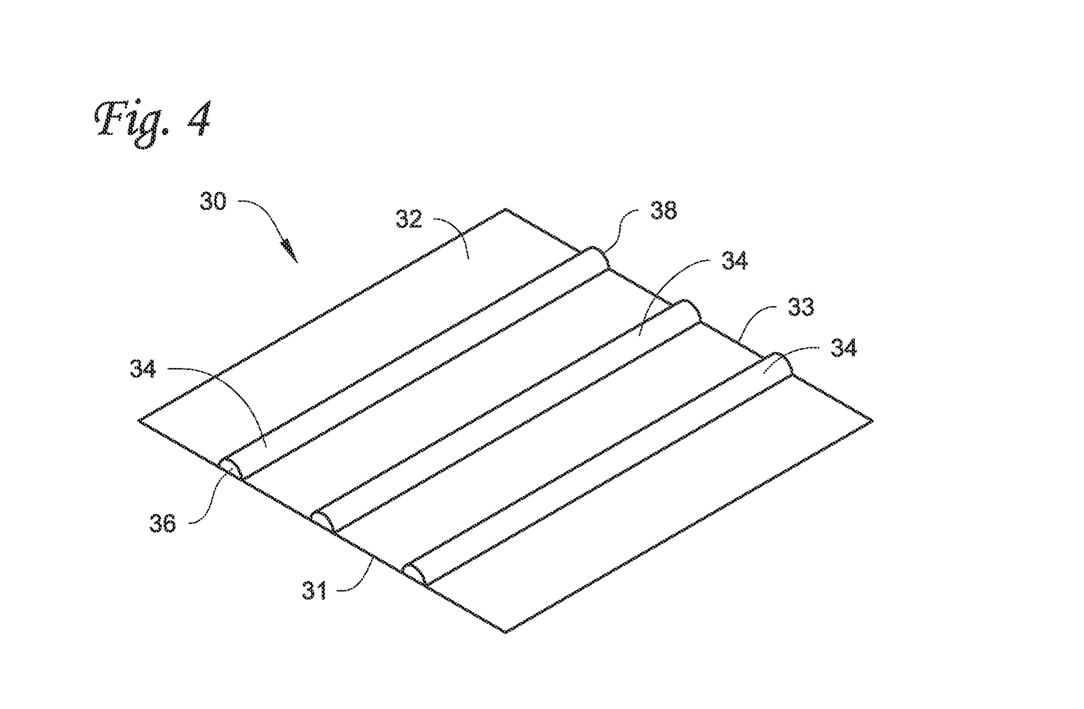
FIG. 4 is a perspective view of one illustrative embodiment of a buttress element as described herein.

One illustrative embodiment of a buttress element as described herein is depicted in FIG. 4. The buttress element 30 has a body 32 in the form of a sheet comprising a thickness, wherein the thickness is measured between a first major surface and a second major surface. The first major surface of the body 32 faces upward and is visible in FIG. 4, while the second major surface of the body 32 faces downward and is, therefore, not seen in FIG. 4. The body 32 is constructed of one or more biocompatible materials. As used herein, a "biocompatible material" is a material that is considered medically acceptable for implantation within a living human body for a period of about one week or more. In some embodiments, the biocompatible material may be bioresorbable.

The buttress element 30 also includes channels 34. Each of the channels 34 extends from a first end to a second end and is located between the first major surface and the second major surface of the body 32. In one or more embodiments such as the embodiment depicted in FIG. 4, the buttress element 30 has a width measured between a first side 31 and a second side 33, and wherein the channel 34 extends from the first side to the second side of the buttress element. Although the buttress element 30 includes three channels 34, one or more embodiments of the buttress elements as described herein may include no channels (see, e.g., FIG. 6 and its corresponding description), one or two channels 34, or four or more channels 34. If two or more channels are provided, the channels may be aligned with each other as seen in FIG. 4, but that alignment is not required.

Each of the channels 34 includes a first opening 36 proximate the first end of the channel 34 that may be used to facilitate insertion of brachytherapy delivery device into the channel as described herein. In one or more embodiments, however, the channels may not include any openings, with the brachytherapy delivery device being inserted into the channel through the buttress material making up the buttress element. In one or more embodiments, the buttress elements described herein that include a channel 34 with a first opening 36 may also include a second opening 38 proximate the second end of the channel 34 (see, e.g., FIG. 4).

Figure 5:
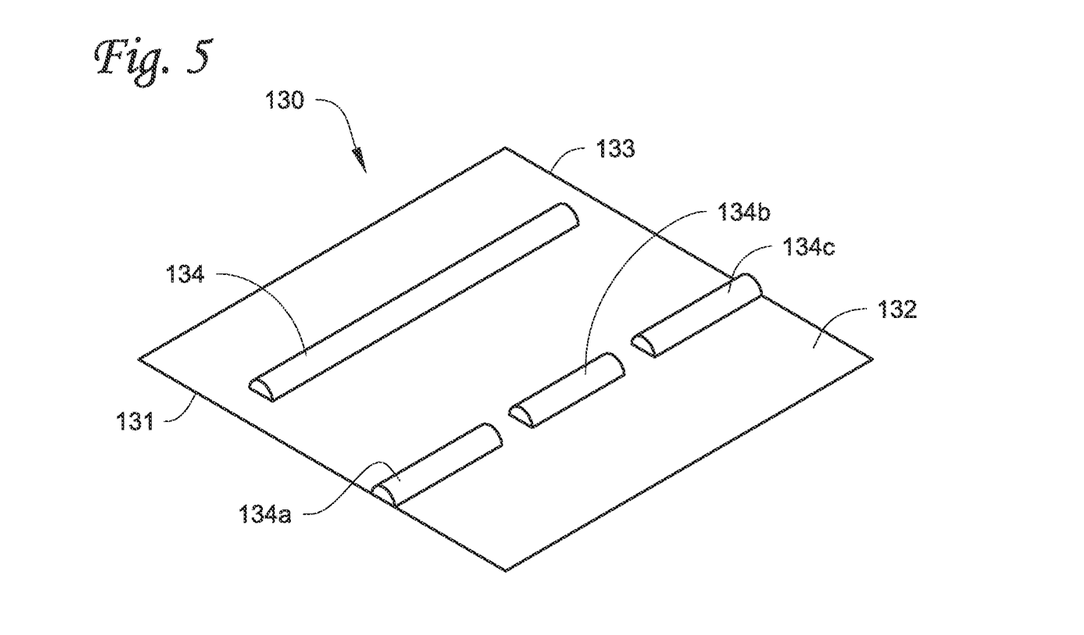
FIG. 5 is a perspective view of another illustrative embodiment of a buttress element as described herein.

Another illustrative embodiment of a buttress element 130 as described herein is depicted in FIG. 5. The buttress element 130 includes a body 132 similar to the body 32 of buttress element 30 depicted in FIG. 4. Differences in the buttress element 132 are, however, found in the construction of the channels provided in buttress element 130. For example, the body 132 of the buttress element 130 has a width measured between a first side 131 and a second side 133, and the channel 134 extends over a channel distance between its ends that is less than the entire width of the body 132 of the buttress element 130. The channels 134a, 134b, and 134c depict other alternative embodiments of channels that may be provided in connection with the buttress elements described herein.

Figure 3:
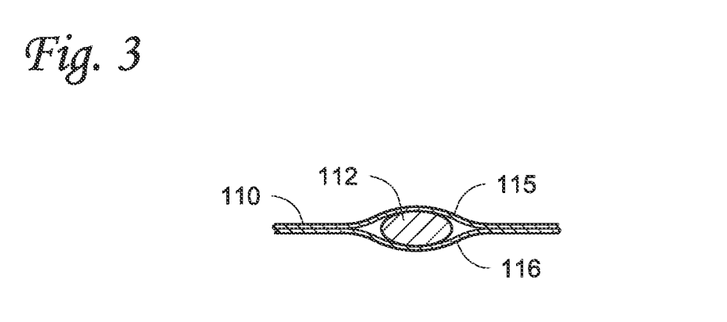
FIG. 3 is a cross-sectional view of one alternative technique for attaching a brachytherapy seed to a carrier line in a brachytherapy device as described herein.

In one or more embodiments, the channels in the buttress elements described herein may be formed between two layers of buttress material attached together along opposing edges of the channel (in, e.g., a construction that may be similar to that depicted in FIG. 3 for the carrier line).

Figure 6:
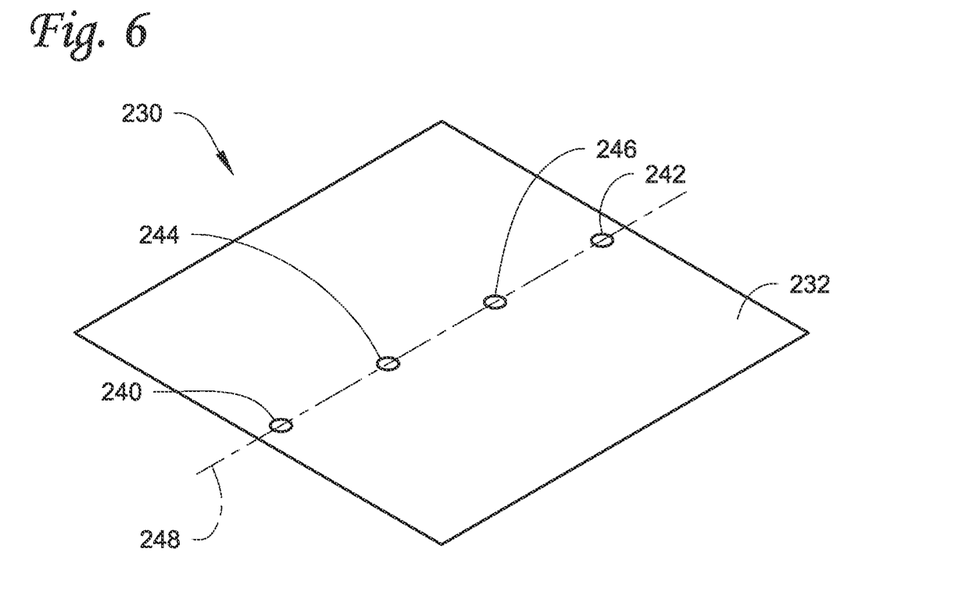
FIG. 6 is a perspective view of another illustrative embodiment of a buttress element as described herein.

Referring to FIG. 6, another alternative illustrative embodiment of a buttress element 230 is depicted, with the buttress element having a body 232 similar to the body 32 of buttress element 30 and the body 132 of buttress element 130. Differences in the buttress element 230 are, however, found in the openings formed through the thickness of the body 232. In particular, the buttress element 230 includes a first opening 240 proximate the first side 231 of the body 232 and a second opening 242 proximate the second side 233 of the body 232.

In one or more embodiments, the buttress element 230 may also include one or more intermediate openings 244 and 246 located between the first side 231 of the body 232 and the second side 233 of the body 232. In one or more embodiments that include one or more intermediate openings, at least one of the one or more intermediate openings may be located along a straight line 248 extending between the first opening 240 and the second opening 242 when the body 232 of the buttress element 230 is in a flat configuration (e.g., laying on a flat surface, etc.). In the illustrative embodiment depicted in FIG. 6, both of the intermediate openings 244 and 246 are located on line 248, but in one or more embodiments, only one of a plurality of intermediate openings may be located on the line 248 extending between the first opening 240 and the second opening 242.

The bodies of buttress elements described herein may, in one or more embodiments, be constructed of one or more layers of buttress material connected to form a single piece body. For example, a buttress element may be formed by two or more layers of buttress material between the clamping members of a surgical stapler, such as that described in U.S. Patent Application Publication No. 2007/0246505.

Any suitable buttress material may be used. Some potentially suitable buttress materials may include, e.g., natural or synthetic materials and may include, but are not limited to, bovine pericardium, collagen absorbable hemostat, vicryl (VICRYL, by Ethicon, Inc., Somerville, N.J.), ePTFE (expanded polytetrafluoroethylene), and those mentioned in U.S. Pat. No. 5,468,253 (Bezwada et al.), U.S. Pat. No. 6,592,597 (Grant et al.), U.S. Pat. No. 6,656,193 (Grant et al.) and U.S. Pat. No. 6,704,210 (Myers), U.S. Patent Application Publication No. 2007/0246505 (Pace-Floridia et al.); and Downey et al., "Functional Assessment of a New Staple Line Reinforcement in Lung Resection," *J. Surg. Res.*, 131 (1): 49-52 (March 2006). Those skilled in the art would recognize other suitable materials that may be used as a buttress material.

Figure 7:
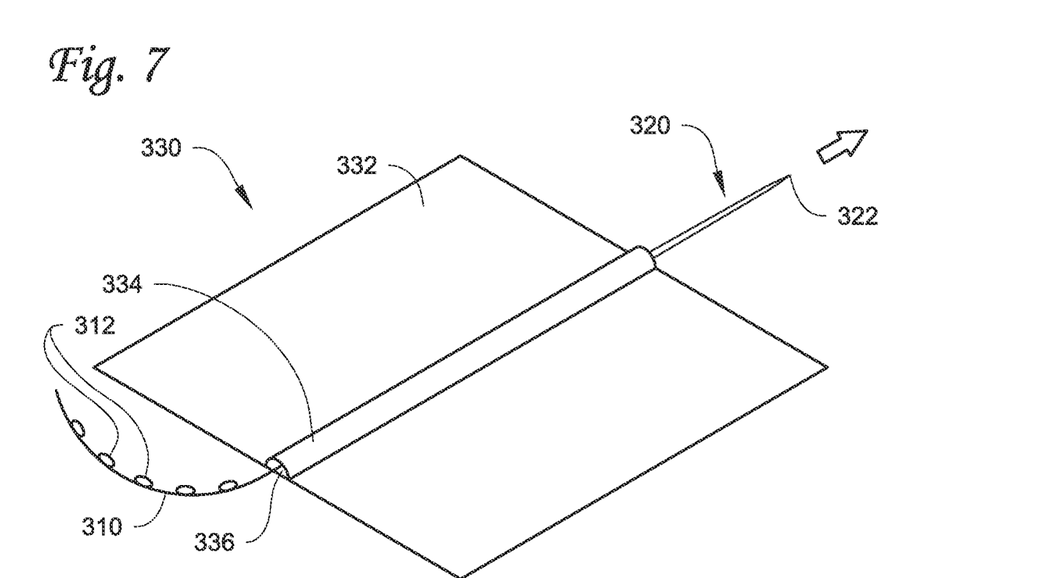
FIG. 7 is a perspective view depicting one illustrative embodiment of assembling a brachytherapy delivery device and a buttress element as described herein.

Referring now to FIG. 7, one illustrative embodiment of a method of assembling a brachytherapy delivery device with a buttress element is depicted. In particular, the brachytherapy delivery device includes a stylet 320 (having a tip 322) and a carrier line 310 including brachytherapy seeds 312 attached thereto. The buttress element 330 includes a body 332 and a channel 334 similar to the buttress elements and channels described in connection with FIGS. 4 and 5.

The illustrative method of assembling buttress element 330 with radioactive material of the brachytherapy delivery device involves advancing the tip 322 of the stylet 320 of the brachytherapy delivery device into the opening 336 in the channel 334, followed by advancing the stylet 320 through the channel 334 until at least a portion of the radioactive material (e.g., the brachytherapy seeds 312) is located in the channel 334. When the radioactive material is located in the channel 334, the method further includes separating the carrier line 310 from the stylet 320.

As a result, the buttress element 330 is assembled with the radioactive brachytherapy seeds 312 on the carrier line 310 in the channel 334. In that assembled state, the buttress element 330 can be secured at a surgical site in accordance with known methods to provide both support and radiation therapy.

If the buttress element includes openings in place of a channel (as depicted and described in connection with FIG. 6), one illustrative embodiment of a method of assembling the buttress element with radioactive material in a brachytherapy delivery device as described herein includes inserting the brachytherapy delivery device through a first opening in a buttress element. The brachytherapy delivery device may be inserted through the opening in the buttress element using the stylet. The brachytherapy delivery device is then advanced until at least a portion of the radioactive material passes through the first opening. The stylet of the brachytherapy delivery device is then advanced through a second opening formed in the buttress element such that the carrier line extends between the first opening and the second opening. The method further includes separating the carrier line from the stylet.

After assembly with a buttress element, the carrier line (carrying the radioactive material) can be codelivered with the buttress element to a resection site (e.g., at a staple line). In one or more embodiments, the assembly (i.e., the buttress element and carrier line) is adapted to be codelivered in an endoscopic procedure through an endoscopic passage to a resection site.

The buttress materials and carrier materials may be provided in any form that is suitable for delivery using a stapler as described herein. Delivering the buttress element to a resection site may include rolling the buttress element into a roll having a longitudinal axis that is generally aligned along an edge of the clamping members of a stapler. The buttress material and/or carrier elements may be attached to the delivery device (e.g., a stapler, etc.) by any suitable technique, e.g., clamps, ties, hooks, clips (e.g., Weck clips, etc.), sutures, adhesives, tapes, etc. Examples of some potentially suitable stapler-based delivery systems for buttress material may be described in one or more of the following documents: U.S. Pat. No. 5,752,965 (Francis et al.); U.S. Pat. No. 5,810,855 (Rayburn et al.); U.S. Pat. No. 6,939,358 (Palacios et al.); US Patent Application Publication US 2004/0093029 (Zubiket al.); etc.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of assembling a buttress element with radioactive material, the method comprising:
   inserting a brachytherapy delivery device into only one channel in a buttress element,
      wherein the brachytherapy delivery device comprises a carrier line and a stylet, the carrier line comprising a length extending between a first end and a second end, wherein radioactive material is distributed along the carrier line, and the stylet extending from a base to a tip, wherein the first end of the carrier line is attached to the stylet proximate the base of the stylet,
      and wherein the buttress element comprises a body in the form of a sheet comprising a thickness, wherein the thickness is measured between a first major surface and a second major surface, and wherein the body is constructed of one or more biocompatible materials, and wherein the channel is formed in the body, the channel extending from a first end to a second end, and wherein the channel is located between the first major surface and the second major surface of the buttress element;
   advancing the tip of the stylet of the brachytherapy delivery device through the channel until at least a portion of the radioactive material is located in the channel; and
   separating the carrier line from the stylet after advancing the tip of the stylet through the channel, such that the radioactive material in the channel is located between the first major surface and the second major surface of the body.

2. A method according to claim 1, wherein the buttress element comprises a width measured between a first side and a second side, and wherein the channel extends from the first side to the second side of the buttress element.

3. A method according to claim 1, wherein the buttress element comprises a width measured between a first side and a second side, and wherein the channel extends over a channel distance that is less than the entire width of the buttress element.

4. A method according to claim 1, wherein the channel comprises a first opening proximate the first end of the channel.

5. A method according to claim 4, wherein the channel comprises a second opening proximate the second end of the channel.

6. A method according to claim 1, wherein the channel is formed between two layers of buttress material attached together along opposing edges of the channel.

7. A method according to claim 1, wherein the buttress element comprises a plurality of channels formed in the body, wherein each channel of the plurality of channels extends from a first end to a second end and is located between the first major surface and the second major surface of the body.

8. A method according to claim 7, wherein the plurality of channels are aligned with each other.

9. A method according to claim 1, wherein the one or more biocompatible materials comprises bioresorbable material.

10. A method of assembling a buttress element with radioactive material, the method comprising:
   inserting a brachytherapy delivery device into a channel in a buttress element,
      wherein the brachytherapy delivery device comprises a carrier line and a stylet, the carrier line comprising a length extending between a first end and a second end, wherein radioactive material is distributed along the carrier line in a plurality of radioactive seeds, and the stylet extending from a base to a tip, wherein the first end of the carrier line is attached to the stylet proximate the base of the stylet,
      and wherein the buttress element comprises a body in the form of a sheet comprising a thickness, wherein the thickness is measured between a first major surface and a second major surface, and wherein the body is constructed of one or more biocompatible materials, and wherein the channel is formed in the body, the channel extending from a first end to a second end, and wherein the channel is located between the first major surface and the second major surface of the buttress element;
   advancing the tip of the stylet of the brachytherapy delivery device through the channel until at least some radioactive seeds of the plurality of radioactive seeds are located in the channel; and separating the carrier line from the stylet after advancing the tip of the stylet through the channel such that the radioactive seeds located in the channel are retained in the channel between the first major surface and the second major surface of the body.

11. A method according to claim 10, wherein the buttress element comprises a width measured between a first side and a second side, and wherein the channel extends from the first side to the second side of the buttress element.

12. A method according to claim 10, wherein the buttress element comprises a width measured between a first side and a second side, and wherein the channel extends over a channel distance that is less than the entire width of the buttress element.

13. A method according to claim 10, wherein the channel comprises a first opening proximate the first end of the channel.

14. A method according to claim 10, wherein the channel is formed between two layers of buttress material attached together along opposing edges of the channel.

15. A method according to claim 10, wherein the buttress element comprises a plurality of channels formed in the body, wherein each channel of the plurality of channels extends from a first end to a second end and is located between the first major surface and the second major surface of the body.

16. A method of assembling a buttress element with radioactive material, the method comprising:
inserting a brachytherapy delivery device into a channel in a buttress element,
wherein the brachytherapy delivery device comprises a carrier line and a stylet, the carrier line comprising a length extending between a first end and a second end, wherein radioactive material is distributed along the carrier line, and the stylet extending from a base to a tip, wherein the first end of the carrier line is attached to the stylet proximate the base of the stylet, and wherein the buttress element comprises a body in the form of a sheet comprising a thickness, wherein the thickness is measured between a first major surface and a second major surface, and wherein the body is constructed of one or more biocompatible materials, and wherein the channel is formed in the body, the channel extending from a first end to a second end, wherein the channel is located between the first major surface and the second major surface of the buttress element, and further wherein the channel is formed between two layers of buttress material attached together along opposing edges of the channel;
advancing the tip of the stylet of the brachytherapy delivery device through the channel until at least a portion of the radioactive material is located in the channel; and
separating the carrier line from the stylet after the radioactive material is located in the channel.

17. A method according to claim 16, wherein the buttress element comprises a width measured between a first side and a second side, and wherein the channel extends from the first side to the second side of the buttress element.

18. A method according to claim 16, wherein the buttress element comprises a width measured between a first side and a second side, and wherein the channel extends over a channel distance that is less than the entire width of the buttress element.

19. A method according to claim 16, wherein the channel comprises a first opening proximate the first end of the channel.

20. A method according to claim 16, wherein the buttress element comprises a plurality of channels formed in the body, wherein each channel of the plurality of channels extends from a first end to a second end and is located between the first major surface and the second major surface of the body.

* * * * *